United States Patent
Manning

Patent Number: 5,723,785
Date of Patent: Mar. 3, 1998

[54] HAND MUSCLE TENSION MEASURING APPARATUS

[76] Inventor: Michael R. Manning, 10875 Crestmont Ave., Philadelphia, Pa. 19154

[21] Appl. No.: 799,378

[22] Filed: Feb. 14, 1997

[51] Int. Cl.$^6$ .................................................. A63B 21/02
[52] U.S. Cl. .................. 73/379.03; 73/379.02; 482/48
[58] Field of Search ............... 73/379.01–379.03; 482/44, 47, 48, 49; 128/774, 782

[56] References Cited

U.S. PATENT DOCUMENTS

| | | | |
|---|---|---|---|
| 1,204,437 | 11/1916 | Heinze | 482/48 |
| 2,784,592 | 3/1957 | Newman | 73/379.02 |
| 3,357,702 | 12/1967 | Van Saders | 482/49 |
| 3,570,849 | 3/1971 | Ratchford | 482/49 |
| 3,738,651 | 6/1973 | Norman et al. | 73/379.03 X |
| 4,226,412 | 10/1980 | Panepinto | 482/49 |
| 5,062,625 | 11/1991 | Vonk | 482/48 |
| 5,078,388 | 1/1992 | Dempsey, Jr. | 482/49 |
| 5,136,911 | 8/1992 | Wyss | 482/48 X |
| 5,147,256 | 9/1992 | Silagy | 482/49 X |
| 5,157,970 | 10/1992 | Lewis, Jr. | 73/379.02 |
| 5,170,663 | 12/1992 | Kovacevic | 73/379.02 |
| 5,317,916 | 6/1994 | Kovacevic | 73/379.03 |
| 5,445,582 | 8/1995 | Brown | 482/44 X |
| 5,451,191 | 9/1995 | Benken | 482/47 |
| 5,613,923 | 3/1997 | Anliker | 482/44 X |

*Primary Examiner*—Elizabeth L. Dougherty

[57] ABSTRACT

A new Hand Muscle Tension Measuring Apparatus for providing a therapeutic hand exercise aid and for obtaining an objective reading of finger muscle tension during rehabilitation. The inventive device includes a T-member, a support member slidably engaging the longitudinal portion of the T-member, a plurality of tension transducers positioned within the support member, a corresponding plurality of resilient loops connected to the tension transducers, and a display screen electronically coupled to the tension transducers to display the tension from each individual finger.

9 Claims, 3 Drawing Sheets

HAND MUSCLE TENSION MEASURING APPARATUS

BACKGROUND OF THE INVENTION

1. Field of the Invention

The present invention relates to Tension Measuring Devices and more particularly pertains to a new Hand Muscle Tension Measuring Apparatus for providing a therapeutic hand exercise aid and for obtaining an objective reading of finger muscle tension during rehabilitation.

2. Description of the Prior Art

The use of Tension Measuring Devices is known in the prior art. More specifically, Tension Measuring Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Tension Measuring Devices include U.S. Pat. No. 4,625,732; U.S. Pat. No. 5,329,813; U.S. Pat. No. 5,317,916; U.S. Pat. No. 5,299,457; U.S. Pat. No. 4,407,295 and U.S. Pat. No. 5,435,315.

While these devices fulfill their respective, particular objectives and requirements, the aforementioned patents do not disclose a new Hand Muscle Tension Measuring Apparatus. The inventive device includes a T-member, a support member slidably engaging the longitudinal portion of the T-member, a plurality of tension transducers positioned within the support member, a corresponding plurality of resilient loops connected to the tension transducers, and a display screen electronically coupled to the tension transducers to display the tension from each individual finger.

In these respects, the Hand Muscle Tension Measuring Apparatus according to the present invention substantially departs from the conventional concepts and designs of the prior art, and in so doing provides an apparatus primarily developed for the purpose of providing a therapeutic hand exercise aid and for obtaining an objective leading of finger muscle tension during rehabilitation.

SUMMARY OF THE INVENTION

In view of the foregoing disadvantages inherent in the known types of Tension Measuring Devices now present in the prior art, the present invention provides a new Hand Muscle Tension Measuring Apparatus construction wherein the same can be utilized for providing a therapeutic hand exercise aid and for obtaining an objective reading of finger muscle tension during rehabilitation.

The general purpose of the present invention, which will be described subsequently in greater detail, is to provide a new Hand Muscle Tension Measuring Apparatus apparatus and method which has many of the advantages of the Tension Measuring Devices mentioned heretofore and many novel features that result in a new Hand Muscle Tension Measuring Apparatus which is not anticipated, rendered obvious, suggested, or even implied by any of the prior art Tension Measuring Devices, either alone or in any combination thereof.

To attain this, the present invention generally comprises a T-member, a support member slidably engaging the longitudinal portion of the T-member, a plurality of tension transducers positioned within the support member, a corresponding plurality of resilient loops connected to the tension transducers, and a display screen electronically coupled to the tension transducers to display the tension from each individual finger.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Hand Muscle Tension Measuring Apparatus apparatus and method which has many of the advantages of the Tension Measuring Devices mentioned heretofore and many novel features that result in a new Hand Muscle Tension Measuring Apparatus which is not anticipated, rendered obvious, suggested, or even implied by any of the prior art Tension Measuring Devices, either alone or in any combination thereof.

It is another object of the present invention to provide a new Hand Muscle Tension Measuring Apparatus which may be easily and efficiently manufactured and marketed.

It is a further object of the present invention to provide a new Hand Muscle Tension Measuring Apparatus which is of a durable and reliable construction.

An even further object of the present invention is to provide a new Hand Muscle Tension Measuring Apparatus which is susceptible of a low cost of manufacture with regard to both materials and labor, and which accordingly is then susceptible of low prices of sale to the consuming public, thereby making such Hand Muscle Tension Measuring Apparatus economically available to the buying public.

Still yet another object of the present invention is to provide a new Hand Muscle Tension Measuring Apparatus which provides in the apparatuses and methods of the prior art some of the advantages thereof, while simultaneously overcoming some of the disadvantages normally associated therewith.

Still another object of the present invention is to provide a new Hand Muscle Tension Measuring Apparatus for providing a therapeutic hand exercise aid and for obtaining an objective reading of finger muscle tension during rehabilitation.

Yet another object of the present invention is to provide a new Hand Muscle Tension Measuring Apparatus which includes a T-member, a support member slidably engaging the longitudinal portion of the T-member, a plurality of tension transducers positioned within the support member, a corresponding plurality of resilient loops connected to the tension transducers, and a display screen electronically coupled to the tension transducers to display the tension from each individual finger.

Still yet another object of the present invention is to provide a new Hand Muscle Tension Measuring Apparatus that is useful for measuring and charting a patient's progress following an injury or disease to the hand, wrist or forearm areas.

Even still another object of the present invention is to provide a new Hand Muscle Tension Measuring Apparatus that may be adapted for interactive computer simulations such as virtual reality systems and computer games.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
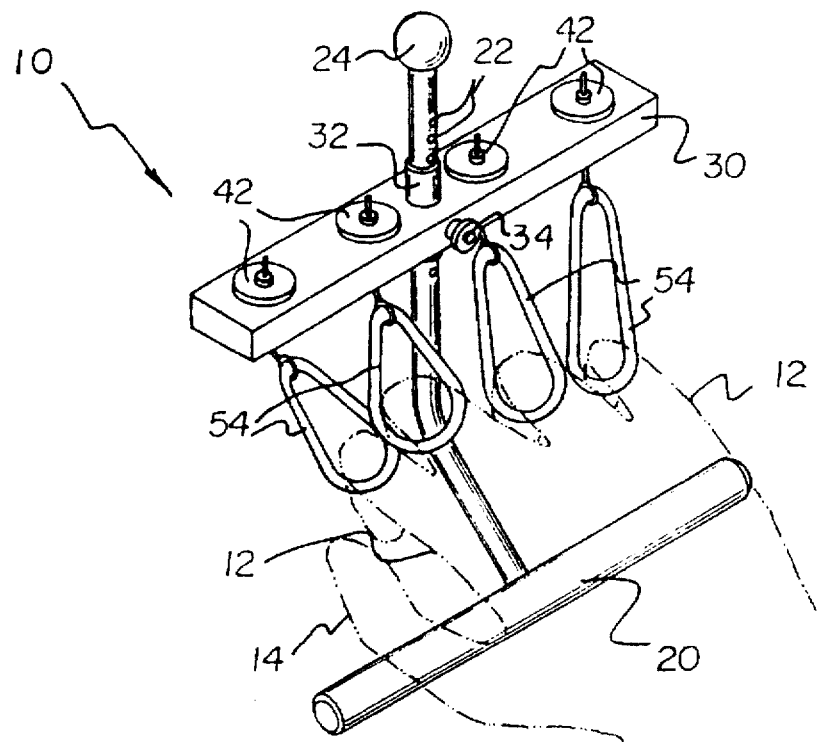
FIG. 1 is a rear upper side perspective view of a new Hand Muscle Tension Measuring Apparatus according to the present invention.
Figure 2:
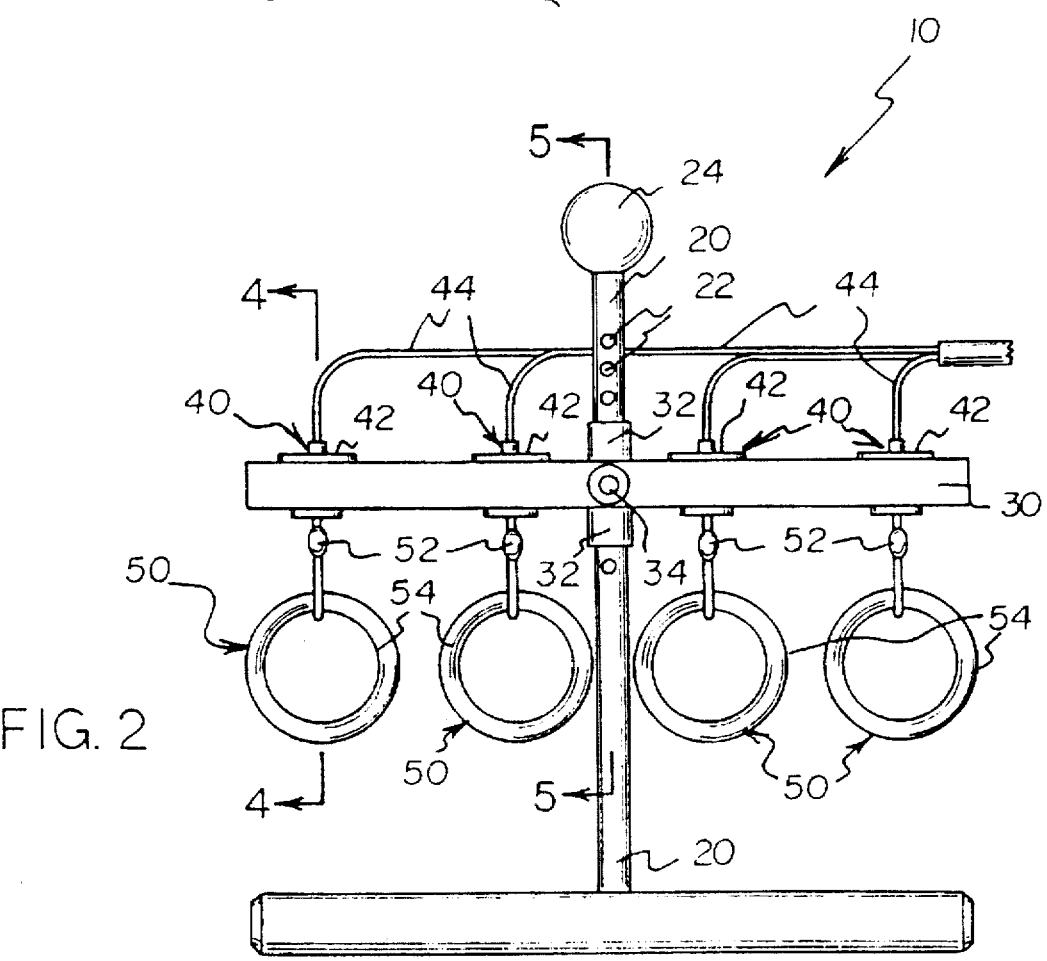
FIG. 2 is a rear view of the present invention.

With reference now to the drawings, and in particular to FIGS. 1 through 6 thereof, a new Hand Muscle Tension Measuring Apparatus embodying the principles and concepts of the present invention and generally designated by the reference numeral 10 will be described.

More specifically, it will be noted that the Hand Muscle Tension Measuring Apparatus 10 comprises a T-member 20, a support member 30 slidably engaging the longitudinal portion of the T-member 20, a plurality of tension transducers 42 positioned within the support member 30, a corresponding plurality of resilient loops 54 connected to the tension transducers 42, and a display screen 62 electronically coupled to the tension transducers 42 to display the tension from each individual finger 12.

As best illustrated in FIGS. 1 through 3 and 5, it can be shown that the T-member 20 has a knob 24 at the end opposite of the traverse portion. A thumb 14 from a user engages the traverse portion as shown in FIG. 1.

Figure 5:
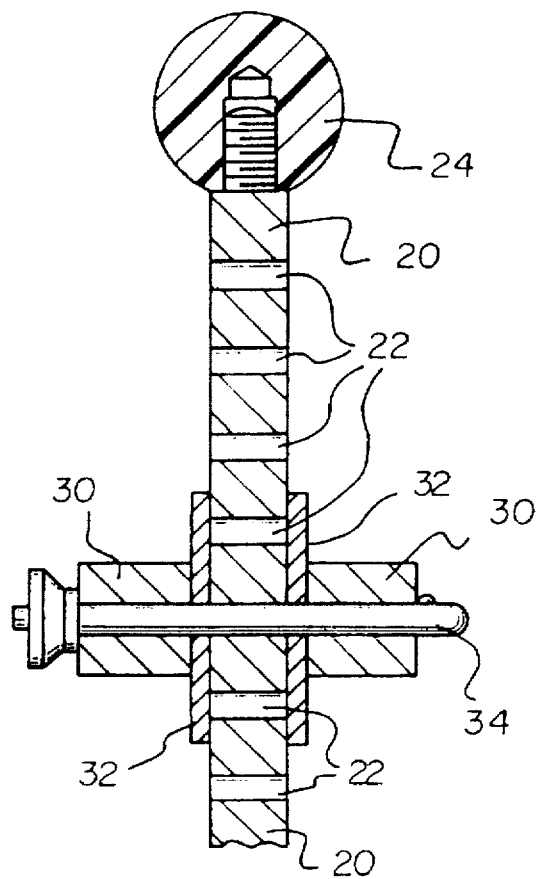
FIG. 5 is a cross sectional view taken along line 5—5 of FIG. 2.

As shown in FIGS. 1 through 5, the support member 30 is slidably coupled traversely to the T-member 20 along the longitudinal portion. The T-member 20 preferably has a plurality of apertures 22 along the longitudinal portion as best shown in FIG. 5. A pin 34 slidably projects through the support member 30 and is received by the aperture 22 for positioning the support member 30 along the T-member 20.

Figure 6:
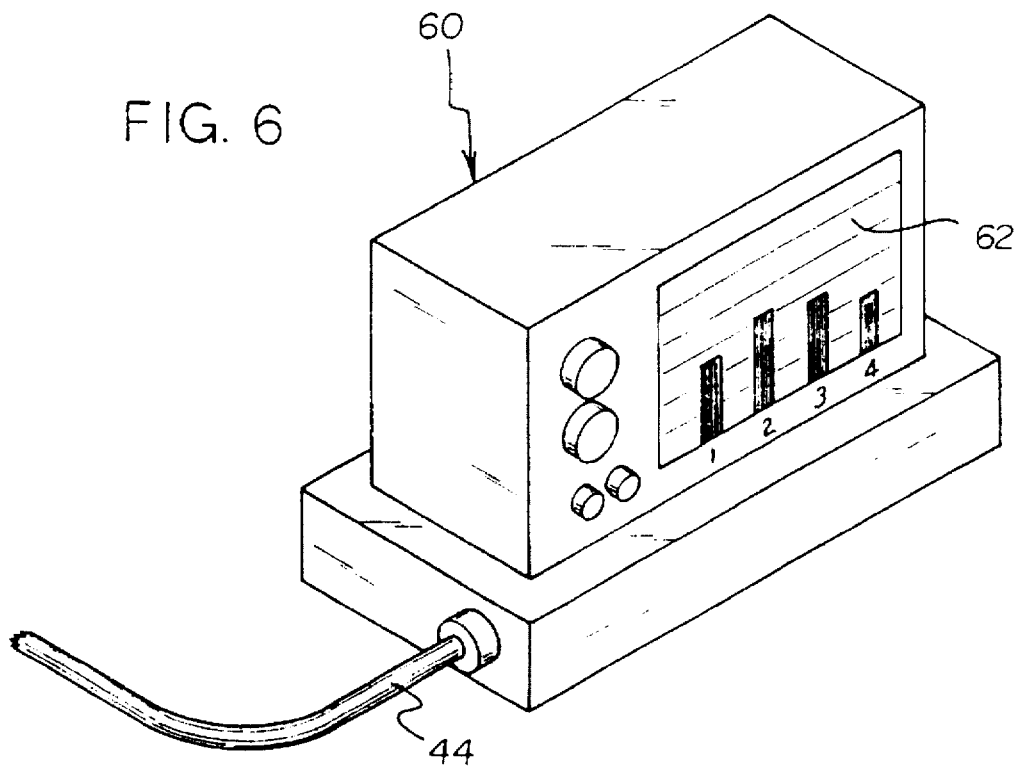
FIG. 6 is an upper front side perspective view of the display means.

As shown in FIGS. 1 through 4, at least one finger tension measuring means 40 is positioned within the support member 30. The finger tension measuring means 40 is constructed from a tension transducer 42. The tension transducer 42 is electrically coupled to a display means 60 which displays the tension of each the finger 12 as shown in FIG. 6 of the drawings. The display means 60 preferably has a display screen 62 electronically coupled to the tension transducer 42 which displays the individual reading of each tension transducer 42 as the fingers 12 pull downwardly upon the resilient loops 54.

Figures 3, 4:
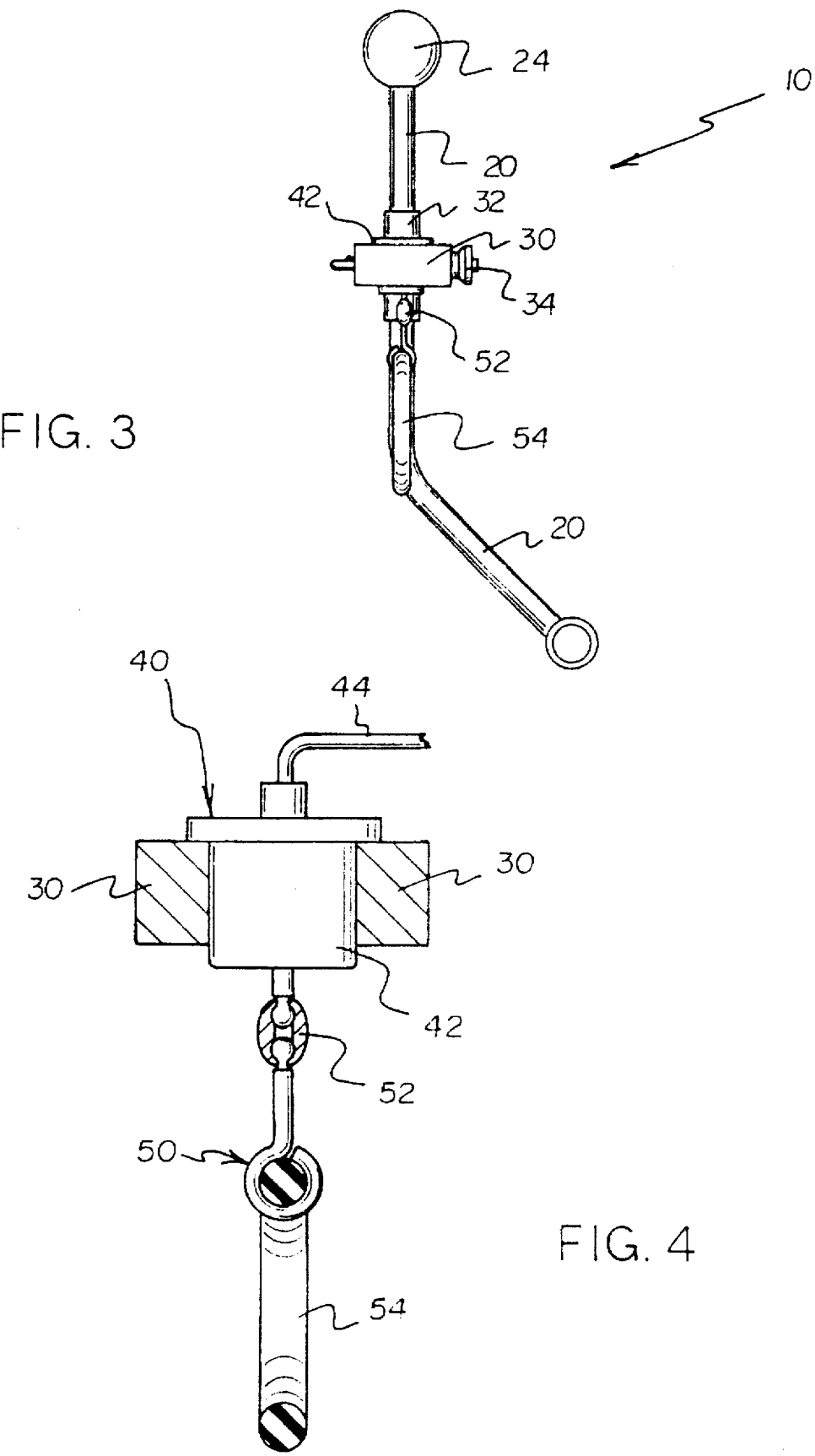
FIG. 3 is a side view of the present invention.
FIG. 4 is a cross sectional view taken along line 4—4 of FIG. 2.

As shown in FIGS. 1 through 4, a finger connecting means 50 is coupled to the finger tension measuring means 40 for engaging a finger 12 of a user. The finger connecting means 50 has a swivel joint 52 coupled to the tension transducer 42 as best shown in FIG. 4 of the drawings. A resilient loop 54 is coupled to the swivel joint 52 opposite of the tension transducer 42, where the resilient loop 54 receives the finger 12 for determining the tension of the finger 12.

In use, the user positions his or her thumb 14 around the traverse portion of the T-member 20. The user's remaining fingers 12 are thereafter positioned within the corresponding resilient loop 54. The user then grasps the resilient loops 54 attempting to bring the fingers 12 together. The tension transducer 42 determines the amount of downward force applied to the resilient loop 54 and electronically sends the measurement through a cable 44 to the display screen 62. The display screen 62 displays the amount of force applied by each individual finger 12 thereby allowing medical personal to evaluate the user's recovery rate from an injury. The present invention may also be utilized as an exercise tool by allowing the user to individually work each finger 12 while being able to monitor the progress made to each finger 12.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A hand muscle tension measuring apparatus comprising:
   a T-shaped member having a longitudinal portion and a transverse portion for being engaged by the thumb of a user;
   a support member slidably coupled to the longitudinal portion of said T-member in a transverse relationship to the longitudinal portion;
   four finger tension measuring means positioned within said support member; and
   a finger connecting means coupled to said finger tension measuring means for engaging a finger of a user, said finger connecting means comprising four finger engaging structures each including a swivel joint rotatably coupled to a said finger tension measuring means, and a flexibly resilient loop coupled to said swivel joint opposite of said finger tension measuring means for receiving a finger of a user such that said tension measuring means is pullable by the finger in a direction towards the transverse portion of the T-shaped member to measure the tension-producing force between the thumb and each individual finger of the user.

2. A hand muscle tension measuring apparatus comprising:
   a T-shaped member having a longitudinal portion and a transverse portion for being engaged by the thumb of a user;
   a support member slidably coupled to the longitudinal portion of said T-member in a transverse relationship to the longitudinal portion;
   at least one finger tension measuring means positioned within said support member; and
   a finger connecting means coupled to said finger tension measuring means for engaging a finger of a user;
   wherein:
   said T-member includes a plurality of apertures along the longitudinal portion; and
   a pin slidably projects through said support member received by said aperture for fixedly positioning said support member along said T-member.

3. The hand muscle tension measuring apparatus of claim 2 wherein said finger tension measuring means comprises a tension transducer electrically coupled to a display means which displays the tension generated by each said finger.

4. The hand muscle tension measuring apparatus of claim 2 wherein said finger connecting means comprises:
   a swivel joint coupled to said tension transducer; and
   a resilient loop coupled to said swivel joint opposite of said tension transducer, where said resilient loop receives said finger.

5. The hand muscle tension measuring apparatus of claim 3 wherein said display means comprises a display screen electronically coupled to said tension transducer.

6. A Hand Muscle Tension Measuring Apparatus comprising:
   a T-shaped member having a longitudinal portion and a transverse portion for being engaged by the thumb of a user, said T-shaped member having a knob at the end opposite of the traverse portion;
   a support member slidably coupled to the longitudinal portion of said T-member in a transverse relationship to the longitudinal portion;
   at least one finger tension measuring means positioned within said support member; and
   a finger connecting means coupled to said finger tension measuring means for engaging a finger of a user;
   wherein:
   said T-member includes a plurality of apertures along the longitudinal portion; and
   a pin slidably projects through said support member received by said aperture for positioning said support member along said T-member.

7. The hand muscle tension measuring apparatus of claim 6 wherein said finger tension measuring means comprises a tension transducer electrically coupled to a display means which displays the tension of each said finger.

8. The hand muscle tension measuring apparatus of claim 6 wherein said finger connecting means comprises:
   a swivel joint coupled to said tension transducer; and
   a resilient loop coupled to said swivel joint opposite of said tension transducer, where said resilient loop receives said finger.

9. The hand muscle tension measuring apparatus of claim 7 wherein said display means comprises a display screen electronically coupled to said tension transducer.

* * * * *